United States Patent [19]

Douglas et al.

[11] 4,152,452

[45] May 1, 1979

[54] METHOD OF TOPICALLY TREATING INFLAMMATION

[75] Inventors: George H. Douglas, Malvern; Norman J. Santora, Roslyn, both of Pa.

[73] Assignee: William H. Rorer, Inc., Fort Washington, Pa.

[21] Appl. No.: 839,959

[22] Filed: Oct. 6, 1977

[51] Int. Cl.² ............................................ A61K 31/275
[52] U.S. Cl. ............................................ 424/304
[58] Field of Search ................................ 424/304

[56] References Cited

U.S. PATENT DOCUMENTS 3,279,907  10/1966  Lindner .................................. 71/2.3

OTHER PUBLICATIONS

Chem. Abst., 77 —61456q (1973).
J.A.C.S., 79 —1236 (1957).

Primary Examiner—Stanley J. Friedman

[57] ABSTRACT

This invention describes a method of treating inflammation in warmblooded animals by topically administering an effective amount of benzylamine and its derivatives.

7 Claims, No Drawings

METHOD OF TOPICALLY TREATING INFLAMMATION

SUMMARY OF THE INVENTION

This invention describes the pharmaceutical compositions and method of treating warmblooded animals for the relief of inflammation and associated pain and fever by the topical administration of benzylamine and its derivatives.

BACKGROUND OF THE INVENTION

Continuous studies have been carried out during the last decade to develop drugs which would significantly inhibit the development of inflammation and relief of pain as well as the pain and fever associated with it. While much of this effort has been carried out in the steroidal field, there have been compounds developed which are non-steroidal such as the alkanoic acids derived from biphenyl, stilbene, naphthalene and various heteryl rings. While many of these compounds have been found to be effective, they have had the drawback of causing various side effects or being effective only on a specific disorder.

We have unexpectedly found that benzylamine and its derivatives have pharmacological properties which are useful for the relief and inhibition of inflammation conditions when administered topically.

We have also found that these compounds are effective in the treatment of inflammation and control of arthritic conditions associated with inflammation.

DESCRIPTION AND PREFERRED EMBODIMENTS

This invention describes a new method of treating inflammation in warmblooded animals by the topical administration of a compound having the structural formula as shown in FIG. I.

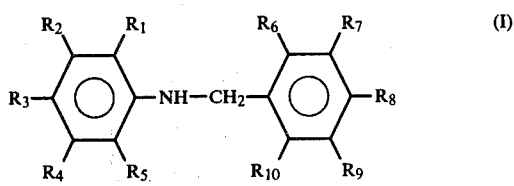

where:
$R_1$, $R_2$, $R_3$, $R_4$, $R_5$, $R_6$, $R_7$, $R_8$, $R_9$ and $R_{10}$ may be the same or different and are:
hydrogen,
alkyl,
cyano,
nitro,
amino,
haloloweralkoxy,
haloloweralkyl,
halo,
loweralkoxy,
acyl,
acyloxy,
thio,
acylthio,
loweralkylthio,
loweralkylsulfinyl,
loweralkylsulfonyl and
hydroxy;

$R_3$ and $R_8$ may also be cycloalkyl, cycloalkenyl, aryl and heteroloweralkylidenyl.

The more preferred compounds for a method of topically treating inflammation embrace those compounds of the Formula II:

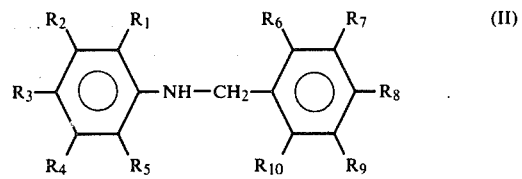

where:
$R_1$, $R_2$, $R_4$, $R_5$, $R_6$, $R_7$, $R_9$ and $R_{10}$ are
hydrogen,
alkyl,
alkoxy,
halo,
haloloweralkyl and
hydroxy;
$R_3$ and $R_8$ are
hydrogen,
alkyl,
alkoxy,
halo,
haloloweralkyl,
hydroxy,
phenyl and
cyclohexyl.

In the descriptive portions of this invention, the following definitions apply:

"alkyl" refers to a loweralkyl hydrocarbon group containing from 1 to about 7 carbon atoms which may be straight chained or branched;

"alkenyl" refers to an unsaturated or partially unsaturated hydrocarbon group containing from 2 to about 7 carbon atoms which may be straight chained or branched;

"cycloalkyl" refers to a hydrocarbon ring having up to about 7 carbon atoms;

"cycloalkenyl" refers to a partially unsaturated hydrocarbon ring having up to about 7 carbon atoms;

"aryl" refers to any benzenoid aromatic group but preferably phenyl;

"acyl" refers to any organic radical derived from an organic acid by the removal of its hydroxyl group such as formyl, acetyl, propionyl, 3-carboxy-2-propenoyl, camphoryl, benzoyl, toluoyl or heteroyl such as pyridinoyl, piperidonyl, thenoyl, etc.

"alkoxy" refers to a loweralkoxy group containing from 1 to about 6 carbon atoms which may be straight chained or branched;

"heteroloweralkylidenyl" refers to a loweralkylidenyl hydrocarbon group containing from about 2 to 5 carbon atoms and having one or more hetero atoms in the chain selected from O, N or S, such as piperidinyl, morpholinyl, etc.

Representative heteryl rings include such as thienyl, furyl, pyridyl, pyrazinyl, pyrimidinyl, pyridazinyl, triazinyl, isoxazolyl, isothiazolyl, pyrrolyl, imidazolyl, pyrazolyl, pyranyl, 2H-pyrrolyl, imidazolidinyl, imidazolinyl, pyrazolidinyl, pyrrolidinyl, pyrrolinyl, piperidyl, piperazinyl, morpholinyl.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as:

hydrochloric acid,
hydrobromic acid,
sulfuric acid,
nitric acid,
phosphoric acid,
methane sulfonic acid,
benzene sulfonic acid,
acetic acid,
propionic acid,
malic acid,
succinic acid,
glycolic acid,
lactic acid,
salicylic acid,
benzoic acid,
nicotinic acid,
phthalic acid,
stearic acid,
oleic acid,
abietic acid, etc.

Representative compounds of this invention which are particularly useful include:
N-benzylaniline
N-(o-hydroxybenzyl)aniline
N-(3-hydroxybenzyl)aniline
N-p-hydroxybenzylaniline
N-benzyl-hydroxyaniline
N-benzyl-o-hydroxyaniline
N-benzyl-m-hydroxyaniline
N-benzyl-p-hydroxyaniline
N-benzyl-dihydroxyaniline
N-benzyl-2,3-dihydroxyaniline
N-benzyl-2,4-dihydroxyaniline
N-benzyl-2,5-dihydroxyaniline
N-benzyl-2,6-dihydroxyaniline
N-benzyl-3,4-dihydroxyaniline
N-benzyl-3,5-dihydroxyaniline
N-benzyl-trihydroxyaniline
N-benzyl-2,3,4-trihydroxyaniline
N-benzyl-2,4,6-trihydroxyaniline
N-(hydroxybenzyl)-hydroxyaniline
N-(o-hydroxybenzyl)-o-hydroxyaniline
N-(m-hydroxybenzyl)-o-hydroxyaniline
N-(p-hydroxybenzyl)-o-hydroxyaniline
N-(o-hydroxybenzyl)-m-hydroxyaniline
N-(m-hydroxybenzyl)-m-hydroxyaniline
N-(p-hydroxybenzyl)-m-hydroxyaniline
N-(o-hydroxybenzyl)-p-hydroxyaniline
N-(m-hydroxybenzyl)-p-hydroxyaniline
N-(p-hydroxybenzyl)-p-hydroxyaniline
N-(dihydroxybenzyl)-dihydroxyaniline
N-(2,3-dihydroxybenzyl)-o-hydroxyaniline
N-(2,4-dihydroxybenzyl)-o-hydroxyaniline
N-(2,5-dihydroxybenzyl)-o-hydroxyaniline
N-(2,6-dihydroxybenzyl)-o-hydroxyaniline
N-(3,4-dihydroxybenzyl)-o-hydroxyaniline
N-(3,5-dihydroxybenzyl)-o-hydroxyaniline
N-(3,4,5-trihydroxybenzyl)-o-hydroxyaniline
N-(2,4,6-trihydroxybenzyl)-o-hydroxyaniline
N-(2,4-dihydroxybenzyl)-m-hydroxyaniline
N-(2,4-dihydroxybenzyl)-m-hydroxyaniline
N-(2,5-dihydroxybenzyl)-m-hydroxyaniline
N-(2,6-dihydroxybenzyl)-m-hydroxyaniline
N-(3,4-dihydroxybenzyl)-m-hydroxyaniline
N-(3,5-dihydroxybenzyl)-m-hydroxyaniline
N-(3,4,5-trihydroxybenzyl)-m-hydroxyaniline
N-(2,4,6-trihydroxybenzyl)-m-hydroxyaniline
N-(2,3-dihydroxybenzyl)-p-hydroxyaniline
N-(2,4-dihydroxybenzyl)-p-hydroxyaniline
N-(2,5-dihydroxybenzyl)-p-hydroxyaniline
N-(2,6-dihydroxybenzyl)-p-hydroxyaniline
N-(3,4-dihydroxybenzyl)-o-hydroxyaniline
N-(3,5-dihydroxybenzyl)-p-hydroxyaniline
N-(3,4,5-trihydroxybenzyl)-o-hydroxyaniline
N-(2,4,6-trihydroxybenzyl)-p-hydroxyaniline
N-(o-chlorobenzyl)aniline
N-(m-chlorobenzyl)aniline
N-(p-chlorobenzyl)aniline
N-benzyl-chloroaniline
N-benzyl-o-chloroaniline
N-benzyl-m-chloroaniline
N-benzyl-p-chloroaniline
N-benzyl-dichloroaniline
N-benzyl-2,3-dichloroaniline
N-benzyl-2,4-dichloroaniline
N-benzyl-2,5-dichloroaniline
N-benzyl-2,6-dichloroaniline
N-benzyl-3,4-dichloroaniline
N-benzyl-3,5-dichloroaniline
N-benzyl-trichloroaniline
N-benzyl-2,4,6-trichloroaniline
N-(halobenzyl)-haloaniline
N-(o-chlorobenzyl)-o-chloroaniline
N-(m-chlorobenzyl)-o-chloroaniline
N-(p-chlorobenzyl)-o-chloroaniline
N-(o-chlorobenzyl)-m-chloroaniline
N-(m-chlorobenzyl)-m-chloroaniline
N-(p-chlorobenzyl)-m-chloroaniline
N-(o-chlorobenzyl)-p-chloroaniline
N-(m-chlorobenzyl)-p-chloroaniline
N-(p-chlorobenzyl)-p-chloroaniline
N-(dihalobenzyl)-dihaloaniline
N-(2,3-dichlorobenzyl)-o-chloroaniline
N-(2,4-dichlorobenzyl)-o-chloroaniline
N-(2,5-dichlorobenzyl)-o-chloroaniline
N-(2,6-dichlorobenzyl)-o-chloroaniline
N-(3,4-dichlorobenzyl)-o-chloroaniline
N-(3,5-dichlorobenzyl)-o-chloroaniline
N-(2,4,6-trichlorobenzyl)-o-chloroaniline
N-(2,3-dichlorobenzyl)-m-chloroaniline
N-(2,4-dichlorobenzyl)-m-chloroaniline
N-(2,5-dichlorobenzyl)-m-chloroaniline
N-(2,6-dichlorobenzyl)-m-chloroaniline
N-(3,4-dichlorobenzyl)-m-chloroaniline
N-(3,5-dichlorobenzyl)-m-chloroaniline
N-(2,4,6-trichlorobenzyl)-m-chloroaniline
N-(2,3-dichlorobenzyl)-p-chloroaniline
N-(2,4-dichlorobenzyl)-p-chloroaniline
N-(2,5-dichlorobenzyl)-p-chloroaniline
N-(2,6-dichlorobenzyl)-p-chloroaniline
N-(3,4-dichlorobenzyl)-p-chloroaniline
N-(3,5-dichlorobenzyl)-p-chloroaniline
N-(2,4,6-trichlorobenzyl)-p-chloroaniline
N-(o-fluorobenzyl)aniline
N-(m-fluorobenzyl)aniline
N-(p-fluorobenzyl)aniline N-benzyl-fluoroaniline
N-benzyl-o-fluoroaniline
N-benzyl-m-fluoroaniline
N-benzyl-p-fluoroaniline
N-benzyl-difluoroaniline
N-benzyl-2,3-difluoroaniline
N-benzyl-2,4-difluoroaniline
N-benzyl-2,5-difluoroaniline
N-benzyl-2,6-difluoroaniline
N-benzyl-3,4-difluoroaniline
N-benzyl-3,5-difluoroaniline
N-(p-phenylbenzyl)aniline
N-(p-phenylbenzyl)-haloaniline
N-(p-phenylbenzyl)-o-bromoaniline
N-(p-phenylbenzyl)-m-bromoaniline
N-(p-phenylbenzyl)-p-bromoaniline
N-(p-phenylbenzyl)-dibromoaniline
N-(p-phenylbenzyl)-2,3-dibromoaniline
N-(p-phenylbenzyl)-2,4-dibromoaniline
N-(p-phenylbenzyl)-2,5-dibromoaniline
N-(p-phenylbenzyl)-2,6-dibromoaniline
N-(p-phenylbenzyl)-3,4-dibromoaniline
N-(p-phenylbenzyl)-3,5-dibromoaniline
N-(p-phenylbenzyl)-tribromoaniline
N-(p-phenylbenzyl)-3,4,5-trihydroxyaniline
N-(p-phenylbenzyl)-2,4,6-trihydroxyaniline
N-(phenylbenzyl)chloroaniline
N-(p-phenylbenzyl)-o-chloroaniline
N-(p-phenylbenzyl)-o-fluoroaniline
N-(p-phenylbenzyl)-o-hydroxyaniline
N-(p-phenylbenzyl)-m-chloroaniline
N-(p-phenylbenzyl)-m-fluoroaniline
N-(p-phenylbenzyl)-m-hydroxyaniline
N-(p-phenylbenzyl)-p-chloroaniline
N-(p-phenylbenzyl)-p-fluoroaniline
N-(p-phenylbenzyl)-p-hydroxyaniline
N-(p-cyclohexylbenzyl)-aniline
N-(p-cyclohexylbenzyl)-haloaniline
N-(o-cyclohexylbenzyl)-bromoaniline
N-(p-cyclohexylbenzyl)-o-bromoaniline
N-(p-cyclohexylbenzyl)-m-bromoaniline
N-(p-cyclohexylbenzyl)-p-bromoaniline
N-(p-cyclohexylbenzyl)-dibromoaniline
N-(p-cyclohexylbenzyl)-2,3-dibromoaniline
N-(p-cyclohexylbenzyl)-2,4-dibromoaniline
N-(p-cyclohexylbenzyl)-2,4-dibromoaniline
N-(p-cyclohexylbenzyl)-2,5-dibromoaniline
N-(p-cyclohexylbenzyl)-2,6-dibromoaniline
N-(p-cyclohexylbenzyl)-3,4-dibromoaniline
N-(p-cyclohexylbenzyl)-3,5-dibromoaniline
N-(p-cyclohexylbenzyl)-tribromoaniline
N-(p-cyclohexylbenzyl)-2,4,6-tribromoaniline
N-(p-cyclohexylbenzyl)-chloroaniline
N-(p-cyclohexylbenzyl)-o-chloroaniline
N-(p-cyclohexylbenzyl)-o-fluoroaniline
N-(p-cyclohexylbenzyl)-o-hydroxyaniline
N-(p-cyclohexylbenzyl)-m-fluoroaniline
N-(p-cyclohexylbenzyl)-m-bromoaniline
N-(p-cyclohexylbenzyl)-m-hydroxyaniline
N-(p-cyclohexylbenzyl)-p-fluoroaniline
N-(p-cyclohexylbenzyl)-p-hydroxyaniline The compounds of this invention may be prepared by the following general procedures.

Condensation of an aldehyde derivative with benzaldehyde derivatives of phenyl ketones along the procedures as described by Gillman and Blatt, Organic Synthesis, Coll. Vol. I, 2nd Ed. N.Y. John Wiley and Sons, pages 80–81, yields the benzylideneaniline compounds.

Reduction of the benzylideneaniline compounds such as with sodium borohydride in a suitable solvent yields the final products (I).

The following reaction equation illustrates this synthesis:

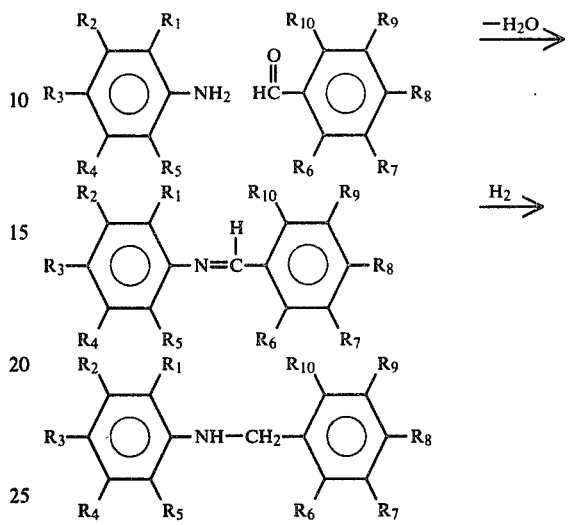

where:
$R_1$, $R_2$, $R_3$, $R_4$, $R_5$, $R_6$, $R_7$, $R_8$, $R_9$ and $R_{10}$ are as described above.

An alternate procedure for preparing certain of the final products of this invention is the reduction of an amide with diborane as follows:

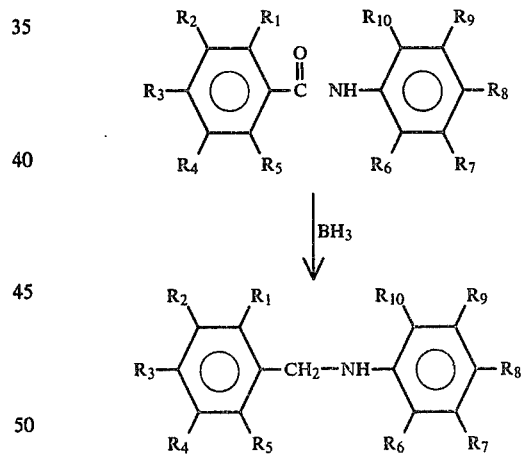

where:
$R_1$, $R_2$, $R_3$, $R_4$, $R_5$, $R_6$, $R_7$, $R_8$, $R_9$ and $R_{10}$ are as described above.

An alternate method for the production of the intermediates used in this synthesis involves the distillation of a product from a neat mixture of a carbonyl compound and an aniline derivative at an elevated temperature and under a reduced pressure.

A still further method of preparing the intermediates which are useful in preparing the final products would be by condensation of a hindered carbonyl compound and an aniline derivative by the azeotropic removal of water.

Approximately desired end products having various substituents can be prepared at various stages of synthesis using suitable reactions in order to convert one group to another. Thus, for example, using conventional methods, a halogen group can be treated under Rosenmund Von Braun conditions to the nitrile compound which in turn can be hydrolyzed to a carboxy. A nitro can be reduced to an amino which can be alkylated to the dialkylamino substituent. A hydroxy compound can be prepared by demethylation of a methoxy substituent. A Sandmeyer type reaction can be carried out on an amino compound to introduce a chloro, bromo, xanthate, hydroxyl or alkoxyl group. The xanthate can then lead to the mercapto by hydrolysis, this in turn can be alkylated to an alkylthio group which can be oxidized to alkylsulfinyl and alkylsulfonyl groups. A thiocyanato group may be removed by catalytic hydrogenation.

In accordance with the present invention, a method of treating inflammation in warmblooded animals is provided which comprises typically administering to the warmblooded animal in need of such treatment an effective amount of a compound of Formula I.

As used herein, the term "treatment" is meant to include both active treatment and preventative or prophylactic treatment.

The present invention also has for its object compositions for treating conditions requiring anti-inflammatory treatment containing at least one of the compounds of Formula I in an amount of about 0.05-5.0% by weight of the composition, preferably from about 0.1-1.0% by weight. These compositions can be in the form of a solution, a cream, a powder, gel, ointment, salve, lotion or milk. They can also constitute makeup products or dermatological cakes containing the ingredients standard to these types of compositions.

The following Examples will further illustrate the formulations containing the compounds of Formula I but are not to be considered as limiting the scope of this invention.

EXAMPLE 1

A. N-(o-Chlorobenzylidene)-2-methyl-3-chloroaniline o-Chlorobenzaldehyde (0.20 mole) is treated with 3-chloro-2-methyl aniline (0.20 mole) with vigorous stirring in a 1 l. Erlenmeyer Flask. After 15 mins., 33 cc of 95% ethanol is added and the reaction mixture is stirred vigorously for an additional 5 mins. The reaction mixture is left standing at room temperature for 10 mins., then it is placed in an ice bath for 0.5 hr. The crystals which formed are collected, washed with 95% ethanol, and air dried. Recrystallization from 85% ethanol gives N-(o-Chlorobenzylidene)-2-methyl-3-chloroaniline. m.p. 83°-85° C.

B. N-(o-Chlorobenzyl)-2-methyl-3-chloroaniline

A suspension of N-(o-chlorobenzylidene)-2-methyl-3-chloroaniline (0.038 mole) is brought to reflux in 100 cc of absolute methanol. An equivalent of sodium borohydride (1.5 g.) is added in portions and refluxing is continued for 15 mins. The reaction mixture is cooled and diluted with an equal volume of cold water to precipitate a solid. This material is collected, washed with H₂O and air dried. Recrystallization from ethanol gives N-(o-Chlorobenzyl)-2-methyl-3-chloroaniline. m.p. 63°-66° C.

EXAMPLE 2

A. N-Benzylideneaniline

Benzaldehyde (0.20 mole) is treated with aniline (0.20 mole) with vigorous stirring in a 1 l. Erlenmeyer Flask. After 15 mins., 33 cc of 95% ethanol is added and the reaction mixture is stirred vigorously for an additional 5 minutes. The reaction mixture is left standing at room temperature for 10 min.; then it is placed in an ice-bath for 0.5 hrs. The crystals which form are collected, washed with 95% ethanol and air-dried. Recrystallization from 85% ethanol gives N-Benzylideneaniline. m.p. 50°-51.5° C.

B. N-Benzylaniline

Following the procedure of Example 1B, but substituting N-benzylideneaniline for N-(p-chlorobenzylidene)-3-chloro-2-methylaniline, there is obtained N-benzylaniline.

EXAMPLE 3

A. N-(o-Hydroxybenzylidene)aniline o-Hydroxybenzaldehyde (0.20 mole) is treated with aniline with vigorous stirring in a 1 l. Erlenmeyer Flask. After 15 mins., 33 cc of 95% ethanol is added and the reaction mixture is stirred vigorously for an additional 5 min. The reaction mixture is left standing at room temperature for 10 min., then it is placed in an ice-bath for 0.5 hr. The crystals which form are collected, washed with 95% ethanol, and air dried. Recrystallization from 85% ethanol yields N-(o-hydroxybenzylidene)aniline. m.p. 47°-49° C.

B. N-(o-Hydroxybenzyl)aniline

Following the procedure of Example 1B, but substituting N-(o-hydroxybenzylidene)aniline in place of N-(o-chlorobenzylidene)-2-methyl-3-chloroaniline, there is obtained N-(o-hydroxybenzyl)aniline.

EXAMPLE 4

A. N-(p-Chlorobenzylidene)-2-methyl-4-chloroaniline

2-Methyl-4-chloroaniline (0.25 mole) and 4-chlorobenzaldehyde (0.25 mole) are ground in a mortar. The mixture is heated, with stirring in a water bath for 1.5 hrs. Distillation at reduced pressure gives N-(p-Chlorobenzylidene)-2-methyl-4-chloroaniline. b.p. 139° C./0.020 mm.

B. N-(p-Chlorobenzyl)-2-methyl-4-chloroaniline

Following the procedure of Example 1B, but substituting N-(p-chlorobenzylidene)-2-methyl-4-chloroaniline in place of N-(o-chlorobenzylidene)-2-methyl-3-chloroaniline, there is obtained N-(p-chlorobenzyl)-2-methyl-4-chloroaniline.

EXAMPLE 5

A. N-(Methylbenzylidene)-p-toluidine p-Toluidine (0.20 mole), acetophenone (0.20 mole), and IRC-50 (weakly acidic) ion exchange resin (0.5 g.) are azeotropically refluxed in toluene (150 cc). The required amount of water is removed after 3 hrs. The solvent is removed on the rotary, and the residue is distilled under reduced pressure to give N-(methylbenzylidene)-p-toluidine. b.p. 129°-37° C./0.05 mm.

B.

Following the procedure of Example 1B but substituting N-(methylbenzylidene)-p-toluidine in place of N-(o-chlorobenzylidene)-2-methyl-3-chloroaniline, there is obtained N-(methylbenzyl)-p-toluidine.

EXAMPLE 6

A. N-(o-Hydroxybenzylidene)-2-methyl-3-chloroaniline o-Hydroxybenzaldehyde (0.20 mole) is treated with 2-methyl-3-chloroaniline (0.20 mole) with vigorous stirring in a 1 l Erlenmeyer Flask. After 15 mins., 33 cc. of 95% ethanol is added and the reaction mixture is stirred vigorously for an additional 45 mins. The reaction mixture is lest standing at room temperature for 10 mins., then it is placed in an ice-bath for 0.5 hr. The crystals which form are collected, washed with 95% ethanol, and air dried. Recrystallization from 85% ethanol gives N-(o-hydroxyenzylidene)-2-methyl-3-chloroaniline. m.p. 95°–97°.

B.

Following the procedure of Example 1B but substituting N-(o-hydroxybenzylidene)-2-methyl-3-chloroaniline in place of N-(o-chlorobenzylidene)-2-methyl-3-chloroaniline there is obtained N-(o-hydroxybenzyl)-2-methyl-3-chloroaniline.

EXAMPLE 7

A. N-(p-Chlorobenzylidene)-2-methyl-3-chloroaniline 2-methyl-3-chloroaniline (0.25 mole) and 4-chlorobenzaldehyde (0.25 mole) are ground in a mortar. The mixture is heated, with stirring in a water bath for 1.5 hours. Distillation at reduced pressure gives N-(p-chlorobenzylidene)-2-methyl-3-chloroaniline; Bp. 139° C./0/020 mm.

B.

Following the procedure of Example 1B but substituting N-(p-chlorobenzylidene)-2-methyl-3-chloroaniline in place of N-(o-chlorobenzylidene)-2-methyl-3-chloroaniline there is obtained N-(p-chlorobenzyl)-2-methyl-3-chloroaniline.

EXAMPLE 8

A. N-[(p-Phenyl)benzylidene]-p-methylaniline p-toluidine (0.20 mole), 4-biphenylaldehyde (0.20 mole), and IRC-50 (weakly acidic) ion exchange resin (0.5 g.) are azeotropically refluxed in toluene (150 cc). The required amount of water is removed after about 3 hours. The solvent is removed on the rotary, and the residue is recrystallized with 95% ethanol to yield N-[(p-phenyl)benzylidene]-p-methylaniline. m.p. 137°–139° C.

B.

Following the procedure of Example 1B but substituting N-[(p-phenyl)benzylidene]-p-methylaniline in place of N-(o-chlorobenzylidene)-2-methyl-3-chloroaniline there is obtained N-[(p-phenylbenzyl]-p-methylaniline.

EXAMPLE 9

A. N-(o-Chlorobenzylidene)-2,3-dichloroaniline 8.1 grams (0.05 mole) of 2,3-dichloroaniline is added to 7.0 grams (0.05 mole) of o-chlorobenzaldehyde. The reaction vessel and contents are thereafter allowed to stand at room temperature for 4 hours. During this period, the reaction mixture becomes a solid crystalline mass. The latter is dissolved in hot benzene and thereafter cooled to room temperature whereupon 2,3-dichloro-N-(o-chlorobenzylidene) aniline precipitates as a crystalline solid and is recovered by filtration. This product is washed with a petroleum hydrocarbon fraction boiling at from 86° to 100° C. (Skellysolve) and air dried. The washed product has a m.p. at 99.5°–105° C.

B.

Following the procedure of Example 1B but substituting 2,3-dichloro-N-(o-chlorobenzylidene)aniline in place of N-(o-chlorobenzylidene)-2-methyl-3-chloroaniline there is obtained 2,3-dichloro-N-(o-chlorobenzyl)aniline.

EXAMPLE 10

A. N-(Benzylidene)-3,5-dichloroaniline

To a reaction flask, equipped with a Dean-Stark trap, is added 3,5-dichloroaniline (16.2 g., 0.10 mole), benzaldehyde (10.6 g., 0.10 mole), p-toluenesulfonic acid monohydrate (0.2 g.), and toluene (100 ml.). The reaction mixture is then warmed to reflux and the water (1.65 ml.) collected by azeotroping. The cooled reaction mixture is treated with charcoal and the filtrate reduced in vacuo to give an amber oil, that crystallizes on standing to give N-(benzylidine)-3,5-dichloroaniline which is recrystallized from pentane. m.p. 52°–53° C.

B.

Following the procedure of Example 1B but substituting N-(benzylidene)-3,5-dichloroaniline in place of N-(o-chlorobenzylidene)-2-methyl-3-chloroaniline there is obtained N-benzyl-3,5-dichloroaniline.

EXAMPLE 11

A. N-(Benzylidene)-3,4-dichloroaniline

Equimolar amounts of 3,4-dichloroaniline and benzaldehyde are stirred together at room temperature to give a nearly quantitative yield of N-(benzylidene)-3,4-dichloroaniline that melts at 62°–5° C. upon recrystallization from ethanol.

B.

Following the procedure of Example 1B but substituting N-(benzylidene)-3,4-dichloroaniline in place of N-(o-chlorobenzylidene)-2-methyl-3-chloroaniline there is obtained N-benzyl-3,4-dichloroaniline.

EXAMPLE 12

Following the procedure of Example 2, the following compounds were prepared:

| Starting Compound | Final Product |
| --- | --- |
| N-(p-phenylbenzylidene)-methylaniline | N-(p-phenylbenzyl)-methylaniline |
| N-(4-chlorobenzylidene)-4-fluoro-2-trifluoromethylaniline | N-(4-chlorobenzyl)-4-fluoro-2-trifluoromethylaniline |
| N-(o-hydroxybenzylidene)-2,4-dimethylaniline | N-(o-hydroxybenzyl)-2,4-dimethylaniline |

-continued

| Starting Compound | Final Product |
| --- | --- |
| N-benzylidene-4-chloroaniline | N-benzyl-4-chloroaniline |
| N-(m-chlorobenzylidene)-p-fluoroaniline | N-(m-chlorobenzyl)-p-flouroaniline |
| N-benzylidene-2-methyl-4-fluoroaniline | N-benzyl-2-methyl-4-fluoroaniline |
| N-(4-bromobenzylidene)-4-fluoro-2-trifluoromethylaniline | N-(4-bromobenzyl)-4-fluoro-2-trifluoromethylaniline |
| N-(p-phenylbenzylidene)aniline | N-(p-phenylbenzyl)aniline |
| N-(3-chloro-4-cyclohexylbenzylidene)-4-bromoaniline | N-(3-chloro-4-cyclohexylbenzyl)-4-bromoaniline |
| N-(4-fluorobenzylidene)-2-trifluoromethylaniline | N-(4-fluorobenzyl)-2-trifluoromethylaniline |
| N-(p-chlorobenzylidene)-p-fluoroaniline | N-(p-chlorobenzyl)-p-fluoroaniline |
| N-(p-chlorobenzylidene)-4-methylaniline | N-(p-chlorobenzyl)-4-methylaniline |
| N-(o-hydroxybenzylidene)-p-bromoaniline | N-(o-hydroxybenzyl)-p-bromoaniline |
| N-(2,6-dichlorobenzylidene)-p-chloroaniline | N-(2,6-dichlorobenzyl)-p-chloroaniline |
| N-benzylidene-o-toluidine | N-benzyl-o-toluidine |
| N-(o-chlorobenzylidene)-3-chloroaniline | N-(o-chlorobenzyl)-3-chloroaniline |
| N-o-hydroxybenzylidene-$\alpha,\alpha\alpha$ trifluorotoluidine | N-(o-hydroxybenzyl)-$\alpha,\alpha,\alpha$-trifluorotoluidine |
| N-benzylideneaniline | N-benzylaniline |
| N-benzylidene-p-ethylaniline | N-benzyl-p-ethylaniline |
| N-(p-chlorobenzylidene)-m-fluoroaniline | N-(p-chlorobenzyl)-m-fluoroaniline |
| N-(o-chlorobenzylidene)-p-fluoroaniline | N-(o-chlorobenzyl)-p-fluoroaniline |
| N-(p-chlorobenzylidene)-m-chloroaniline | N-(p-chlorobenzyl)-m-chloroaniline |
| N-(o-chloro-$\alpha$-methylbenzylidene)-3-chloroaniline | N-(o-chloro-$\alpha$-methylbenzyl)-3-chloroaniline |
| N-(o-chlorobenzylidene)-3-chloro-2-methylaniline | N-(o-chlorobenzyl)-3-chloro-2-methylaniline |
| N-(o-hydroxybenzylidene)-2-methyl-3-chloroaniline | N-(o-hydroxybenzyl)-2-methyl-3-chloroaniline |
| N-(p-cyclohexylbenzylidene)-p-toluidine | N-(p-cyclohexylbenzyl)-p-toluidine |
| N-[p-(2-morpholino)benzylidene]-aniline | N-[p-(2-morpholino)benzyl]aniline |
| N-(o-chlorobenzylidene)-2-methyl-4-chloroaniline | N-(o-chlorobenzyl)-2-methyl-4-chloroaniline |
| N-(p-chlorobenzylidene)-2-methyl-3-chloroaniline | N-(p-chlorobenzyl)-2-methyl-3-chloroaniline |
| N-(p-chlorobenzylidene)-2-methyl-4-chloroaniline | N-(p-chlorobenzyl)-2-methyl-4-chloroaniline |

EXAMPLE 13

A cream was prepared as follows:

| | |
| --- | --- |
| N-benzylaniline | 0.5 g. |
| Titanium oxide | 10 g. |
| Red iron oxide | 0.3 g. |
| Yellow iron oxide | 0.2 g. |
| Brown iron oxide | 0.4 g. |
| Chestnut iron oxide | 0.2 g. |

Several stearyl alcohols oxyethylenated with 33 mols of:

| | |
| --- | --- |
| Ethylene oxide | 7 g. |
| Polyglycol stearate | 6 g. |
| Propyl parahydroxybenzoate | 0.2 g. |
| Water, Q.S.P. | 100 g. |

Other creams identical to that described immediately above are prepared by replacing N-benzylaniline with any one of the previously mentioned compounds.

EXAMPLE 14

A dermatological cleansing cake is prepared by mixing together the following components:

| | |
| --- | --- |
| Esters of sodium isothionate and coprafatty acids (sold under the tradename "IGEPON A" having the formula R-COO-CH$_2$-CH$_2$-SO$_3$-Na, wherein R equals fatty acid derivatives having 12-15 carbon atoms) | 75 g. |
| Lanolin derivatives | 22.75 g. |
| N-o-chlorobenzyl-2-methyl-4-chloroaniline | 0.75 g. |

Other dermatological cleansing cakes, identical to the above, are prepared by replacing N-(o-chlorobenzyl)-2-methyl-4-chloroaniline with any one of the aforementioned compounds.

EXAMPLE 15

A powder comprising the following mixture:

| | |
| --- | --- |
| Talc | 99.6 g. |
| Glycerine oleate | 3 g. |

| | |
|---|---|
| Isopropyl myristate | 7 g. |
| N-(o-hydroxybenzyl)-2-methyl-3-chloroaniline | 0.5 g. |
| Perfume | 2 cc. |

Other equally effective powder compositions identical to the above are prepared except that the active ingredient N-(o-hydroxybenzyl)-2-methyl-3-chloroaniline is replaced by any of the other aforementioned compounds.

EXAMPLE 16

An anti-inflammatory composition in milk form having the following composition:

| Ingredient | Weight in grams |
|---|---|
| Hydrogenated, ethoxylate (10 mol) lanolin | 1.8 |
| Triglyceride of fatty acid of coconut | 7.0 |
| Cetylalcohol | 0.6 |
| Stearylalcohol | 0.6 |
| Paraffin oil (lightweight) | 5.0 |
| Stearic acid | 3.0 |
| N-(p-cyclohexylbenzyl)-p-toluidine | 3.75 |
| Demineralized water | 72.2 |
| Triethanolamine | 0.8 |
| Perfume | 0.5 |
| Carboxyvinylpolymer | 2.0 |
| Conservation agent | 2.0 | was manufactured as follows:

A mixture of 1.8 g. hydrogenated, ethoxylated (10 mol) lanolin, 7.0 g. triglyceride of fatty acid of coconut, 0.6 g. cetylalcohol, 0.6 g. stearyl alcohol, 5.0 g. paraffin oil and 3.0 g. of stearic acid is blended at 70° C. After addition of 0.75 g. N-(p-cyclohexylbenzyl)-p-toluidine, 2.0 g. carboxyvinylpolymer in 72.2 g. demineralized water are added at 70° C. with stirring to the resulting suspension. The mixture is stirred for 15 minutes and then cooled. 0.8 g. of triethanolamine and 0.5 g. of perfume are added at 60° C. and 45° C. respectively. The resulting mixture is stirred until cold and a white milk, which is stable at 3,000 Rpm for 1 hour is obtained. Viscosity: 6,000 Cp (Brockfield, Spindel, 5, 10 Rpm).

We claim:

1. A method of treating inflammation in warm-blooded animals comprising the topical administration to said animal of an effective amount of a pharmaceutically-active compound of the formula:

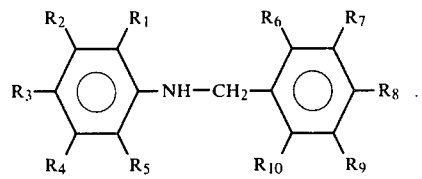

where:

$R_1$, $R_2$, $R_3$, $R_4$, $R_5$, $R_6$, $R_7$, $R_8$, $R_9$ and $R_{10}$ may be the same or different and are:
hydrogen,
alkyl,
cyano,
nitro,
amino,
haloloweralkoxy,
haloloweralkyl,
halo,
loweralkoxy and
hydroxy.

2. The method of topically treating inflammation according to claim 1 where the compound administered is N-(m-trifluoromethylphenyl)-o-hydroxybenzylamine.

3. The method of topically treating inflammation according to claim 1 where the compound administered is N-(2-methyl-3-chlorophenyl)-2-chlorobenzylamine.

4. The method of topically treating inflammation according to claim 1 where the compound administered is N-(p-chlorobenzyl)-2-methyl-3-chloroaniline.

5. The method of topically treating inflammation according to claim 1 where the compound administered is N-(p-chlorobenzyl)-2-methyl-4-chloroaniline.

6. The method of topically treating inflammation according to claim 1 where the compound administered is N-(p-chlorobenzyl)-p-fluoroaniline.

7. The method of topically treating inflammation according to claim 1 where the compound administered is N-(p-phenylbenzyl)-p-toluidine.

* * * * *